United States Patent [19]

Bartmann et al.

[11] 4,056,629
[45] Nov. 1, 1977

[54] PHARMACOLOGICALLY ACTIVE O-ACYL-2,3-DIARYL-3-HALOGENO-ACRYL-ALDOXIMES

[75] Inventors: Wilhelm Bartmann, Neuenhain, Taunus; Gerhard Beck, Frankfurt am Main; Ernold Granzer, Kelkheim, Taunus; Josef Musil, Konigstein, Taunus; Hermann Teufel, Kelkheim, Taunus, all of Germany

[73] Assignee: Hoechst Aktiengesellschaft, Frankfurt am Main, Germany

[21] Appl. No.: 716,277

[22] Filed: Aug. 20, 1976

[30] Foreign Application Priority Data

Aug. 22, 1975 Germany .............................. 2537372

[51] Int. Cl.$^2$ ............................................. A61K 31/15
[52] U.S. Cl. ................................................... 424/327
[58] Field of Search ........................ 424/327, 298, 300

[56] References Cited

U.S. PATENT DOCUMENTS 3,992,538   11/1976   Teufel et al. ......................... 424/327

Primary Examiner—Frederick E. Waddell

Attorney, Agent, or Firm—Curtis, Morris & Safford

[57] ABSTRACT

A medicament consisting of or containing an O-acyl-2,3-diaryl-3-halogeno-acrylaldoxime of the formula I

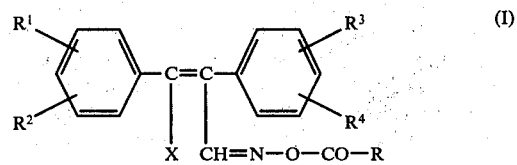

in which X represents a chlorine or bromine atom, R stands for an alkyl, alkenyl, alkoxy, alkenoxy or alkylamino group having from 1 to 12 carbon atoms each, or for an aryl, aryloxy, arylalkyl, arylalkoxy, arylamino or arylalkylamino group substituted optionally by 1 or 2 alkyl groups each having from 1 to 6 carbon atoms, and $R^1$, $R^2$, $R^3$ and $R^4$ are identical or different, each representing a hydrogen atom, a halogen atom or an alkyl or alkoxy group having each from 1 to 6 carbon atoms, a process for preparing them and a method for the treatment of disorders of the purine metabolism.

1 Claim, No Drawings

PHARMACOLOGICALLY ACTIVE O-ACYL-2,3-DIARYL-3-HALOGENO-ACRYL-ALDOXIMES

The invention relates to pharmacologically active O-acyl-2,3-diaryl-3-halogeno-acryl-aldoximes.

The present invention concerns uricosurically and hypouricemically active O-acyl-2,3-diaryl-3-halogeno-acrylaldoximes of the formula I

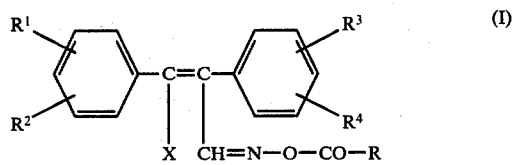

in which X represents a chlorine or bromine atom, R stands for an alkyl, alkenyl, alkoxy, alkenoxy or alkylamino group having each 1 to 12 carbon atoms or for an aryl, aryloxy, arylalkyl, arylalkoxy, arylamino or arylalkylamino group substituted optionally by one or two alkyl groups each having from 1 to 6 carbon atoms, and $R^1$, $R^2$, $R^3$ and $R^4$ are the same or different and each represent a hydrogen atom, a halogen atom or an alkyl or alkoxy group each having from 1 to 6 carbon atoms.

Of the meanings that are appropriate for the substituent R, preference is given in particular to alkyl, alkenyl, alkoxy, alkenoxy and alkylamino groups having from 1 to 6 carbon atoms, such as, for example, methyl, ethyl, propyl, i-propyl, butyl, i-butyl, t-butyl, pentyl, hexyl, as well as the corresponding unsaturated radicals, moreover, methoxy, ethoxy, propoxy, butoxy, and allyloxy. As alkyl and/or alkenyl radicals having up to 12 carbon atoms there may also be mentioned cycloalkyl and/or cycloalkenyl radicals, preferably those having from 5 to 8 carbon atoms, for example, cyclopentyl, cyclohexyl, cyclooctyl, as well as the corresponding radicals with an ethylene double bond.

By aryl there are to be understood in particular naphthyl and phenyl.

Of the meanings mentioned for the substituents $R^1$ to $R^4$, preference is given, among the halogen atoms, to chlorine and bromine, and among the alkyl and alkoxy groups, to those groups having from 1 to 3 carbon atoms, such as methyl, ethyl, propyl and i-propyl.

It has now been found that these compounds act upon the purine metabolism and may therefore be used as medicaments especially for the treatment of disorders of the purine metabolism.

The present invention provides therefore pharmaceutical compositions consisting of, or containing, a compound of the formula I, as well as the use of compounds of the formula I for the treatment of disorders of the purine metabolism.

Compounds of the formula I may be obtained by reacting 2,3-diaryl-3-halogeno-acrylaldoximes of the formula II

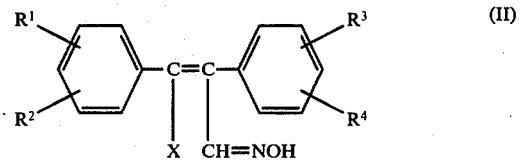

in which X, $R^1$, $R^2$, $R^3$ and $R^4$ are defined as in formula (I) above, in the presence of aprotic solvents, with acylating agents to give O-acyl-2,3-diaryl-3-halogeno-acrylaldoximes of the formula (I).

As acylating agents there are used in particular carboxylic acid halides, carboxylic acid azides, carboxylic acid esters, carboxylic acid anhydrides, arylsulfonyloxy-carboxylic acids, alkylsulfonyloxy-carboxylic acids and ketenes, as well as isocyanates. The acylation is usually carried out at a temperature in the range of from 15° to 60° C, preferably at room temperature; as aprotic solvents there are used, for example, chlorinated hydrocarbons, such as methylene chloride, chloroform or ethylene chloride, ethers, such as diethyl ether, diisopropylether, dimethylether, diethylene-glycol-dimethylether, tetrahydrofuran or dioxan and hydrocarbons, such as pentane, hexane, benzene or toluene.

The 2,3-diaryl-3-halogeno-acryl-aldoximes of the formula (II) used as starting compounds are suitably obtained by converting 2,3-diaryl-3-halogeno-acrylaldehydes of the formula III

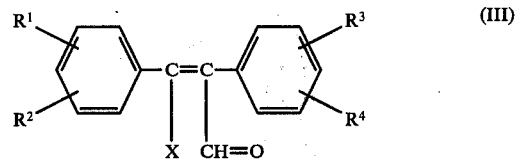

for example, with hydroxylamine-hydrochloride into the oximes. The compounds of the formula III can be prepared in known manner from desoxybenzoins under the conditions of the Vilsmeier reaction (cf., for example, German Offenlegungsschrift No. 2,160,236).

The compounds of the formula I show valuable pharmacological properties, in particular they display a strong hypouricemic and uricosuric activity. In the model situation applied which related to male Wistar rats, this effect was independent from further pharmacological effects, such as the estrogen effect, the effect on the sodium-potassium retention or excretion and the effect on the lipid metabolism. For this reason it is possible to use the above-mentioned substances following the common toxicological and clinical tests as therapeutical compositions for the treatment of different purine metabolism disorders, in particular primary and secondary gout. The survey of the possible indications for which the substances may be used has been given in the following Table 1.

TABLE I

Hyperuricemia: Causes
1. Increased de-novo synthesis of uric acid:
   a. Hyperproduction gout
   b. Lesh-Nyhan syndrome
   c. Lymophoproliferative diseases
   d. Cytostatic therapy
   e. Glycogenosis (type I)
   f. Sickle cell anemia
2. Kidney diseases:
   a) Lowering of the filtration rate, lowering of the tubular secretion or combination of both
     i. Renal insufficiency
     ii. Renal gout
     iii. Lead nephropathy
   b) Competitive secondary lowering of the uric acid excretion
     i. Organic acids, thiazides, paraaminohippuric acid low dosages of the uricosuric agents
     ii. Lactate increase (lactacidose or after an alcohol intake)
     iii. Ketoacidose (diabetic)
     iv. Glycogenosis (type II)
3. Consequences of other metabolism disorders:
   a. Diabetes
   b. Coronary disease TABLE I-continued c. Hypertonia Besides for acting on a lowering of the serum-uric acid and stabilizing the disturbed excretion of uric acid in the urine, as has been indicated in Table 1, the aforementioned substances having the above-specified properties may be used also for normalization of metabolic disorders, in particular disorders of the carbohydrate and lipid metabolisms. Since a hypouricemic and uricosuric effect had been found in the above-mentioned substances, they may, in a manner analogous to other known drugs, be used as possible therapeutical agents for influencing disorders of nucleic acid metabolism and for increasing the antimetabolic effect (6-mercaptopurine).

The specified diseases are present in an incidence of 2 % in the male population and of from 0.2 to 0.7 % in the female population of the civilized countries. The morbidity rate shows a growing tendency. The therapy of the hyperuricemias must be considered not only as a necessary influence on the genuine pathophysiological disturbances, but also as an influence on the risk factor of arteriosclerosis.

The uricosuric and hypouricemic effects were observed by way of experiment on the oxonate rat. In this experimental test arrangement the uricase activity of the rat liver was inhibited by the administration of potassium oxonate, thus producing a gout-like disturbance of the purine metabolism. The effect was tested in the following test arrangement:

1. The influence on the gout-like disturbance of the purine metabolism which had been induced by way of experiment was tested in a 24 hour test. In this test arrangement, the animals are given the substances in a 0.5 % potassium-oxonate solution into the stomach by means of an esophagal sound, after water and fodder had been withheld for 18 hours. During the entire test period, the animals are given the 0.5 % potassium-oxonate solution ad libitum. After 8 hours, they are additionally given 5 ml of water per 100 g of body weight into the stomach, by way of an esophagal sound. After 24 hours urine samples were taken, the animals were killed in a narcosis produced by ether, and the blood and urine were analysed for the content of uric acid. In addition, the creatinine concentration, the sodium, potassium and chloride concentration in the urine and serum samples were determined. The results of these tests have been shown in Table 2 below.

2. The influence on the gout-like metabolism disturbance which had been induced by way of experiment was also examined in a 3-day cycle. For this purpose, the animals (white male Wistar rats) were placed into the metabolism cages 18 hours prior to the start of the experiment. The animals drank water, and they were offered a special fodder mixture to consume ad libitum. The composition of the fodder mixture was as follows: 5 % of fructose, 3% of uric acid, 2 % of potassium oxonate, and 100 mg of synthetic sweetening agent (acesulfame) per 1 kg of body weight. On the first and second days of the experiment, the compositions were administered to the animals, in a 0.5 % potassium-oxonate solution, into the stomach by way of an esophagal sound. The urine samples were examined on the first, second and third days of the experiment, and the serum samples were tested for their uric acid content on the third day of the experiment.

The results of the test of three compositions of the invention have been given in Table 3 below. In Table 4 the results following the application of allopurinol (as comparative substance) have been indicated in the above-mentioned experimental scheme.

TABLE 2

I: Compound having an uricosuric activity (combined with the increase of diuresis and the excretion of sodium). 2-Phenyl-3-bromo-cinnamic aldoxime-O-(N-phenyl)-carbamate (compound of Example 14)

24-Hour test

|  | Uric acid excretion mg/24 hr./100 g b. wt. | | urine pH | Amount of urine excreted ml/24 hr./100 g b. wt. | | Amount of urine Na+ mg/24 hr/100 g b. wt. |
|---|---|---|---|---|---|---|
|  | $\bar{x} \pm SD^{**}$ | % control |  | $\bar{x} + SD$ | % control |  |
| Control group oxonate | 2.98 + 1.09 | 100 | 7.5 + 0.2 | 7.1 + 2.1 | 100 | 0.09 + 0.03 |
| 3 mg/kg | 3.52 + 1.11 | 118 | 7.2 + 0.08* | 9.3 + 3.06 | 130 | 0.11 + 0.02 |

*statistically significant p 0.05 (Scheffe test)
**standard deviation

II: Compound with uricosuric and hypouricemic activity. O-Caprinoyl-2-(4-methoxyphenyl)-3-chloro-p-methoxy-cinnamic aldoxime (compound of Example 8)

24-Hour test

|  | Uric acid excretion mg/24 hr./100 g b. wt. | | Uric acid serum | |
|---|---|---|---|---|
|  | $\bar{x} \pm SD^{**}$ | % control | $\bar{x}$ (mg %) $\pm$ SD | % control |
| Control group oxonate | 2.74 + 1.43 | 100 | 5.41 + 0.66 | 100 |
| 0.3 mg/kg | 3.25 + 1.68 | 118 | 5.00 + 0.54* | 92 |
| 3.0 mg/kg | 2.46 + 1.19 | 89 | 4.81 + 0.74* | 88 |

*statistically significant p 0.05 (U test)
**standard deviation

TABLE 3

|  | Oxonate control group | | | Compound of Example 5 3 mg/kg | | | Compound of Example 6 3 mg/kg | | | Compound of Example 7 3 mg/kg | | |
|---|---|---|---|---|---|---|---|---|---|---|---|---|
| Group parameter | 1st day | 2nd day | 3rd day | 1st day | 2nd day | 3rd day | 1st day | 2nd day | 3rd day | 1st day | 2nd day | 3rd day |
| Urine |  |  |  |  |  |  |  |  |  |  |  |  |
| Uric acid conc. mg % | 42.5 | 42.9 | 48.8 | 38.9 | 32.4 | 34.7 | 33.4 | 32.8 | 32.7 | 36.4 | 31.8 | 31.2 |
| Amount of uric acid mg/24 h | 3.38 | 3.83 | 5.17 | 2.59 | 2.41 | 3.68 | 2.40 | 2.96 | 2.98 | 2.78 | 2.99 | 2.74 |

TABLE 3-continued

|  | Oxonate control group | Compound of Example 5 3 mg/kg | Compound of Example 6 3 mg/kg | Compound of Example 7 3 mg/kg |
|---|---|---|---|---|
| Serum | | | | |
| Uric acid conc. mg % | 5.49 | 4.07* | 3.65* | 4.03* |

*statistically significant p < 0.05 (Duncan test)

TABLE 4

|  | Oxonate control group | | | Allo 50 mg/kg | | | Allo 100 mg/kg | | |
|---|---|---|---|---|---|---|---|---|---|
| Group parameter | 1st day | 2nd day | 3rd day | 1st day | 2nd day | 3rd day | 1st day | 2nd day | 3rd day |
| Urine | | | | | | | | | |
| Uric acid conc. mg % | 11.3 | 23.9 | 36.4 | 11.6 | 18.7 | 31.6 | 12.7 | 19.9 | 28.2 |
| Amount of uric acid mg/24 h | 0.80 | 2.6 | 3.4 | 0.91 | 2.1 | 3.8 | 0.9 | 2.0 | 3.7 |
| Serum | | | | | | | | | |
| Uric acid conc. mg % | | 6.7 | | | 6.2* | | | 5.2* | |

* = statistically significant p < 0.05 (Duncan test)
Allo = Allopurinol

Due to the pharmacological properties found in them, the compounds may be used as medicaments.

They may be administered either as such or in admixture with pharmacologically acceptable carriers. The oral dosage unit form is preferred: For this purpose the active compounds may be mixed with known excipients and brought into a suitable dosage unit form according to known methods, for example, tablets, hard gelatin capsules, aqueous or oily suspensions, or aqueous or oily solutions. Suitable inert carriers are, for example, magnesium carbonate, lactose or corn starch, with the addition of further substances, such as magnesium stearate.

As oily carriers or solvents there may be mentioned in particular vegetable and animal oils, for example, sunflower oil or cod liver oil.

As seen in the experimental pharmacological tests, a single dosage unit in the range of from 0.2 to 1 mg/kg may be considered to be therapeutically effective. A dosage unit contains, for example, from 1 to 200 mg, preferably from 10 to 100 mg, of the compounds of the invention. The dosage is administered once to several times per day.

A special form of application of the compounds of the formula I is to be seen in the combination with other therapeutically effective compounds. The combination with compounds having antihypertensive, diuretic, antidiabetic, cardiovascular, geriatric and psychopharmacological effects is of particular importance.

The following Examples serve to illustrate the invention.

EXAMPLE 1

10 g of 2-(4-methoxyphenyl)-3-chloro-p-methoxy-cinnamic aldoxime were introduced into 50 ml of acetanhydride and were stirred at room temperature. After about 1 hour the total amount of oxime was dissolved. After 2.5 hours, 2-(4-methoxyphenyl)-3-chloro-p-methoxy-cinnamic aldoxime-O-acetate precipitated in a crystalline form and was recrystallized from a mixture of methanol/water. Melting point: 130°–132° C.

EXAMPLE 2

2-(4-Methoxyphenyl)-3-chloro-p-methyl-cinnamic aldoxime-O-acetate was prepared according to Example 1. Melting point: 128°–130° C.

EXAMPLE 3

2-Phenyl-3-chloro-p-ethoxy-cinnamic aldoxime-O-acetate was prepared according to Example 1. Melting point: 118°–119° C.

EXAMPLE 4

3.17 Grams of 2-(4-methoxyphenyl)-3-chloro-p-methoxy-cinamic aldoxime were stirred for 3 hours at room temperature with 30 ml of methylene chloride, 4 g of benzoyl chloride, and 2.5 g of potassium carbonate. The mixture was worked up by diluting it with methylene chloride, then about 30 ml of water were added, the mixture was shaken vigorously, and the methylene chloride phase was separated. After drying and evaporating the solution under reduced pressure, 2-(4-methoxyphenyl)-3-chloro-p-methoxycinnamic aldoxime-O-benzoate was obtained, which was recrystallized from ethanol. Melting point: 146°–147° C.

In an analogous manner, 2-(4-methoxyphenyl)-3-bromo-p-methoxy-cinnamic aldoxime-O-benzoate was obtained, which had a melting point of 134°–135° C.

EXAMPLE 5

In a manner analogous to that described in Example 4, O-benzoyl-2-phenyl-3-bromo-cinnamic aldoxime was prepared, which was recrystallized from isopropanol and had a melting point of 156°–158° C.

EXAMPLE 6

In a manner analogous to that described in Example 4, O-acetyl-2-phenyl-3-bromo-cinnamic aldoxime was prepared, which was recrystallized from isopropanol and had a melting point of 154° C.

EXAMPLE 7

In a manner analogous to that described in Example 4, O-caprinoyl-2-phenyl-3-bromo-cinnamic aldoxime was prepared, which was recrystallized from butylacetate and had a melting point of 122°–124° C.

EXAMPLE 8

In a manner analogous to that described in Example 4, O-caprinoyl-2-(4-methoxyphenyl)-3-chloro-p-methoxy-cinnamic aldoxime was prepared, which was recrystallized from a mixture of ethanol/water. Melting point: 71°–73° C.

EXAMPLE 9

O-Phenylacetyl-2-(4-methoxyphenyl)-3-chloro-p-methoxy-cinnamic aldoxime was prepared according to Example 4. Melting point: 110°–111° C.

EXAMPLE 10

O-Cyclohexanoyl-2-phenyl-3-chloro-p-methyl-cinnamic aldoxime was prepared according to Example 4. Melting point: 122° C.

EXAMPLE 11

O-Cyclohexanoyl-2-phenyl-3-chloro-p-methoxy-cinnamic aldoxime was prepared according to Example 4. Melting point: 112° C.

EXAMPLE 12

2 Grams of phenyl-3-chloro-p-methyl-cinnamic aldoxime were suspended in 20 ml of absolute methylene chloride, to which the equimolar amount of phenyl-isocyanate was added. The reaction solution became clear already after a short-time stirring at room temperature and was allowed to stand for about 12 hours at room temperature. Subsequently the solution was evaporated, and the solid residue was boiled out with methanol. When the filtered methanolic solution became cold, 2-phenyl-3-chloro-p-methyl-cinnamic aldoxime-O-(N-phenyl-carbamate) precipitated in pure white intricated crystals, which melted at 108° C under decomposition.

EXAMPLE 13

In a manner analogous to that of Example 12, 2-phenyl-3-bromo-cinnamic aldoxime-O-(N-3-trifluoromethylphenyl)-carbamate was prepared and was recrystallized from a mixture of acetic ester/cyclohexane. Melting point 128° C.

EXAMPLE 14

In a manner analogous to that of Example 12, 2-phenyl-3-bromo-cinnamic aldoxime-O-(N-phenyl)-carbamate was prepared and was recrystallized from a mixture of acetic ester/cyclohexane. Melting point: 121° C.

EXAMPLE 15

2-Phenyl-3-chloro-p-methoxy-cinnamic aldoxime-O-(N-phenylcarbamate) was prepared according to Example 12. Melting point: 74° C, with decomposition.

EXAMPLE 16

2-(4-Methoxyphenyl)-3-chloro-p-methoxy-cinnamic aldoxime-O-(N-m-trifluoromethylphenyl-carbamate) was prepared according to Example 12. Melting point: 170°–171° C, with decomposition.

EXAMPLE 17

2-Phenyl-3-chloro-p-methyl-cinnamic aldoxime-O-(N-m-trifluoromethylphenyl-carbamate) was prepared according to Example 13. Melting point: 155°–160° C, with decomposition.

EXAMPLE 18

40 Milligrams of 2-phenyl-3-bromo-cinnamic aldoxime-O-(N-phenyl)-carbamate were mixed with 25 to 30 % by weight of lactose as carrier substance, 10 to 15 % by weight of starch as disintegrating agent, and 1 to 5 % by weight of polyvinylpyrrolidone as granulating agent and were pressed into a tablet.

What is claimed is:

1. A method for treating hyperurecemia which comprises orally administering to a patient suffering therefrom a therapeutically effective amount of a compound of the formula

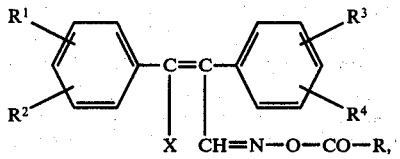

wherein X is chlorine or bromine; R is alkyl, alkenyl, alkoxy, alkenoxy, or alkylamino each having from 1 to 12 carbon atoms, or R is a member selected from the group consisting of phenyl, phenyloxy, phenylalkyl, phenylalkoxy, phenylamino, phenylalkylamino, naphthyl, naphthyloxy, naphthylalkyl, naphthylalkoxy, naphthylamino, and naphthylalkylamino, or R is such a member mono-substituted or di-substituted by alkyl having 1 to 6 carbon atoms; and $R^1$, $R^2$, $R^3$, and $R^4$ are the same or different and are hydrogen, halogen, or alkyl or alkoxy each having from 1 to 6 carbon atoms.

* * * * *